US010586325B2

(12) United States Patent
Cummings et al.

(10) Patent No.: US 10,586,325 B2
(45) Date of Patent: Mar. 10, 2020

(54) DELAMINATION TRACKING SYSTEMS AND METHODS

(71) Applicant: BAE Systems Controls Inc., Endicott, NY (US)

(72) Inventors: Thomas J. Cummings, Endwell, NY (US); Joseph D. Cipollina, Binghamton, NY (US)

(73) Assignee: BAE Systems Controls Inc., Endicott, NY (US)

( * ) Notice: Subject to any disclaimer, the term of this patent is extended or adjusted under 35 U.S.C. 154(b) by 180 days.

(21) Appl. No.: 15/860,064

(22) Filed: Jan. 2, 2018

(65) Prior Publication Data

US 2019/0206039 A1    Jul. 4, 2019

(51) Int. Cl.
| | |
|---|---|
| G06T 7/00 | (2017.01) |
| G01N 21/88 | (2006.01) |
| G06T 7/13 | (2017.01) |
| G06T 7/136 | (2017.01) |
| G06T 7/12 | (2017.01) |

(52) U.S. Cl.
CPC .......... *G06T 7/001* (2013.01); *G01N 21/8851* (2013.01); *G06T 7/12* (2017.01); *G06T 7/13* (2017.01); *G06T 7/136* (2017.01); *G06T 2207/30148* (2013.01); *G06T 2207/30152* (2013.01)

(58) Field of Classification Search
CPC . G06T 7/001; G06T 7/13; G06T 2207/30152; G06T 2207/30148; G06T 7/136; G06T 7/12; G01N 21/8851
See application file for complete search history.

(56) References Cited

U.S. PATENT DOCUMENTS

| | | | | |
|---|---|---|---|---|
| 2010/0158325 A1* | 6/2010 | Piramuthu | ......... | G06K 9/00234 382/118 |
| 2014/0233843 A1* | 8/2014 | Cocca | ................... | G06T 7/0004 382/145 |

* cited by examiner

*Primary Examiner* — Menatoallah Youssef
(74) *Attorney, Agent, or Firm* — Scully Scott Murphy & Presser PC; Scott J. Asmus

(57) ABSTRACT

A method of determining delamination in a transistor is disclosed including loading a grey scale image of an transistor into memory, generating a black and white image based on the loaded grey scale image, identifying boundaries within the generated black and white image, cropping the black and white image based on the identified boundaries, identifying at least one feature in the cropped black and white image based on the identified boundaries, normalizing the cropped black and white image based on an attribute of the identified at least one feature, cropping the grey scale image based on the normalized black and white image, comparing the cropped grey scale image to a baseline grey scale image of the transistor, and determining a change in a percentage of delamination of the transistor between the baseline grey scale image and the cropped grey scale image based on the comparison.

20 Claims, 11 Drawing Sheets

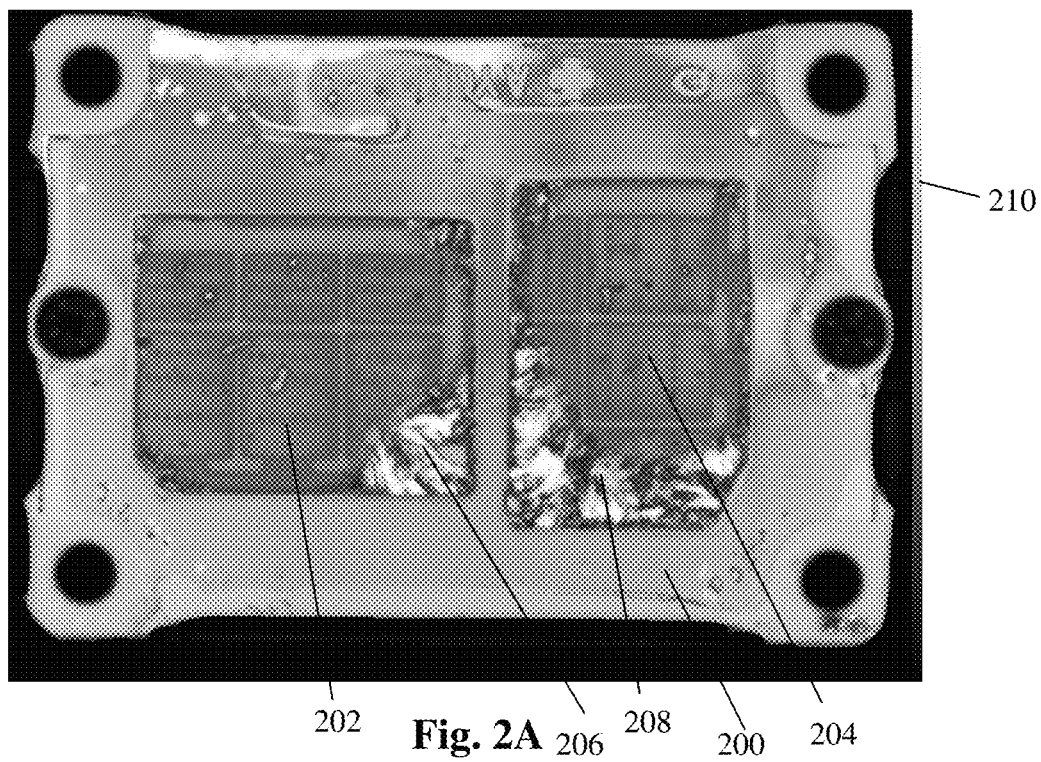
202   Fig. 2A 206  208  200  204
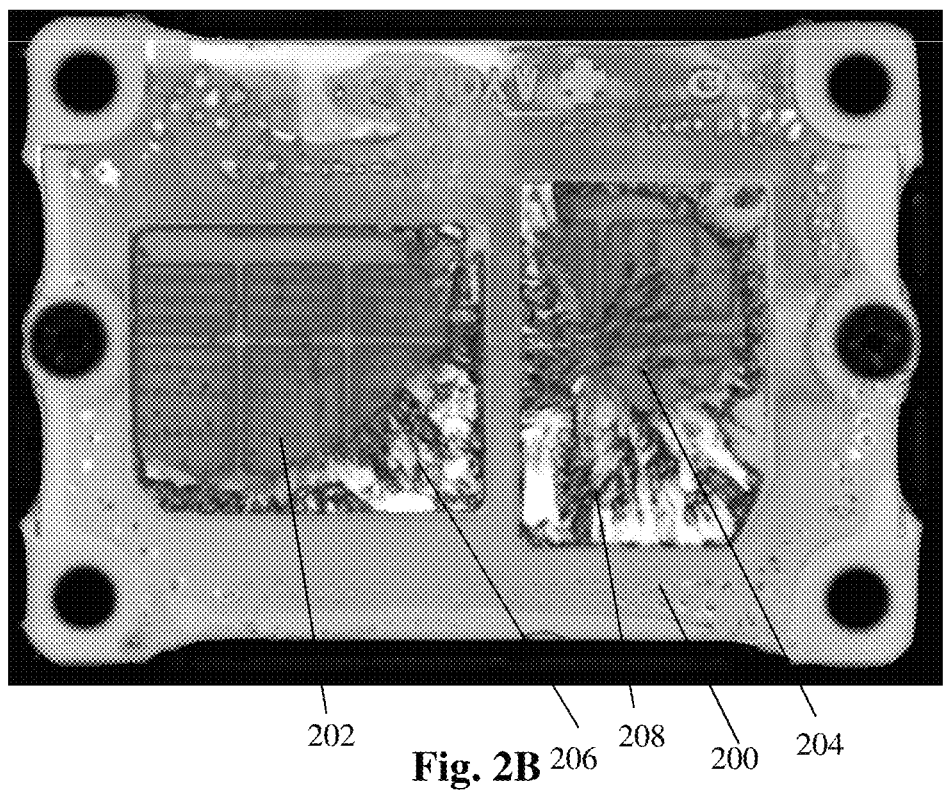
202   Fig. 2B 206  208  200  204

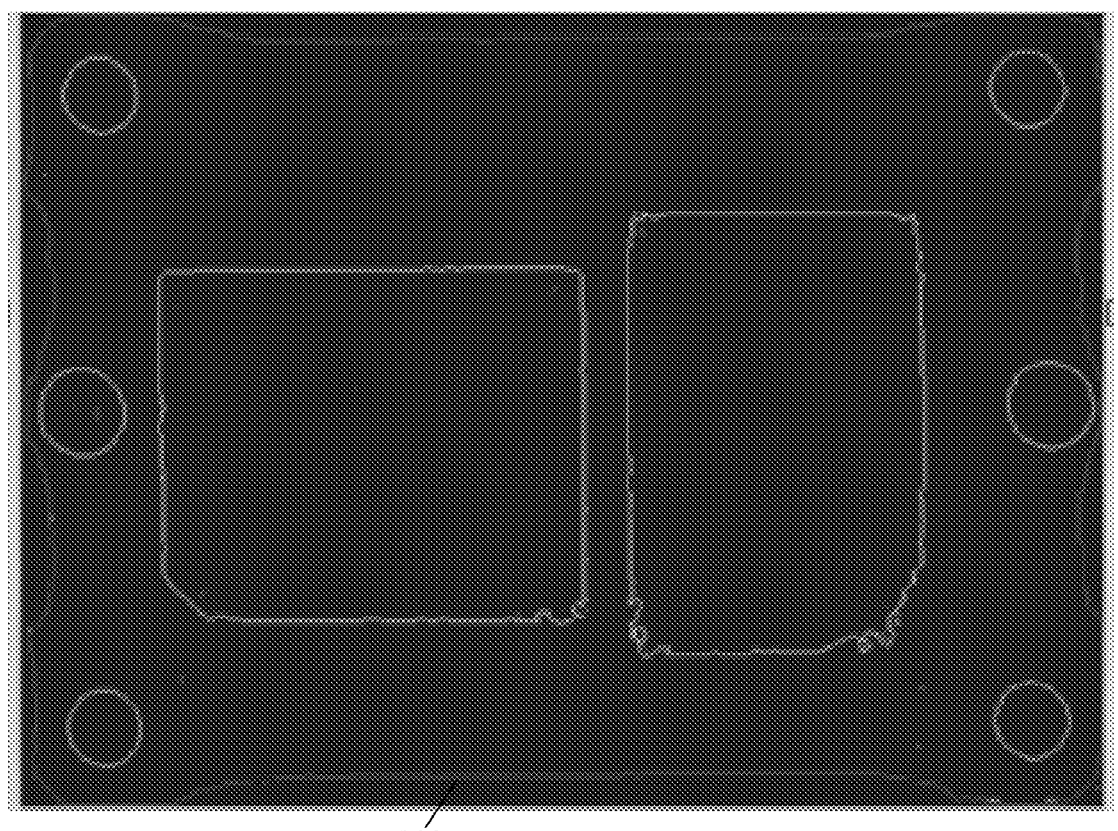
900  Fig. 9
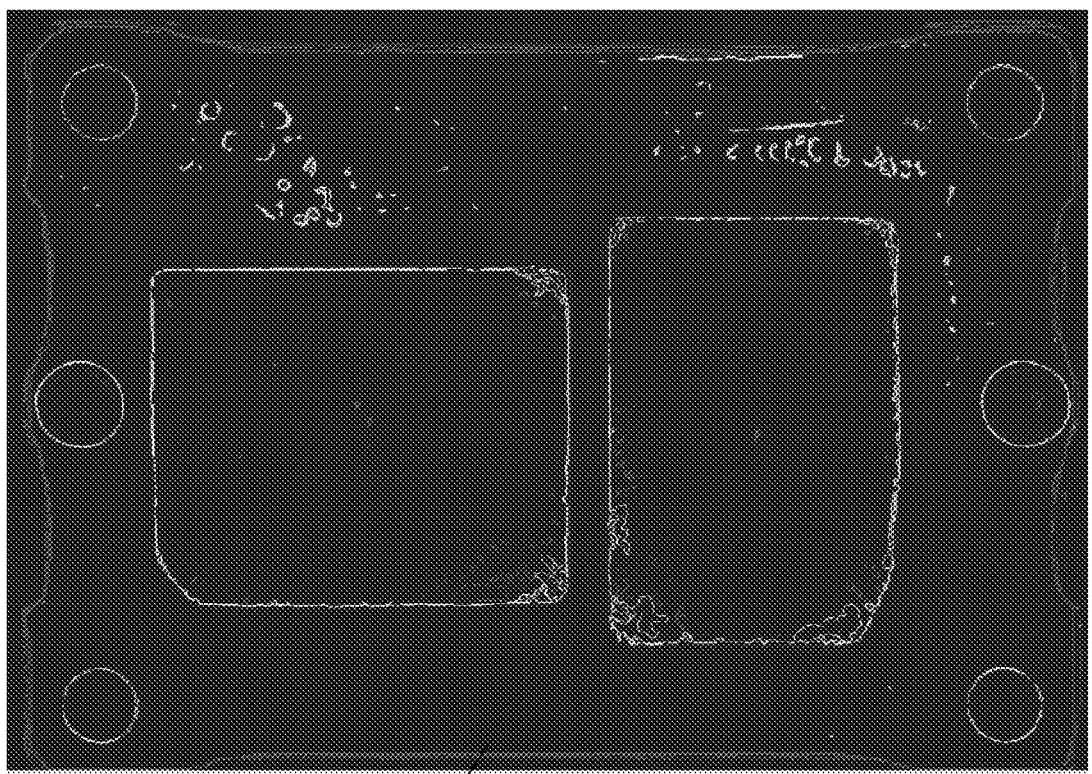
1000  Fig. 10

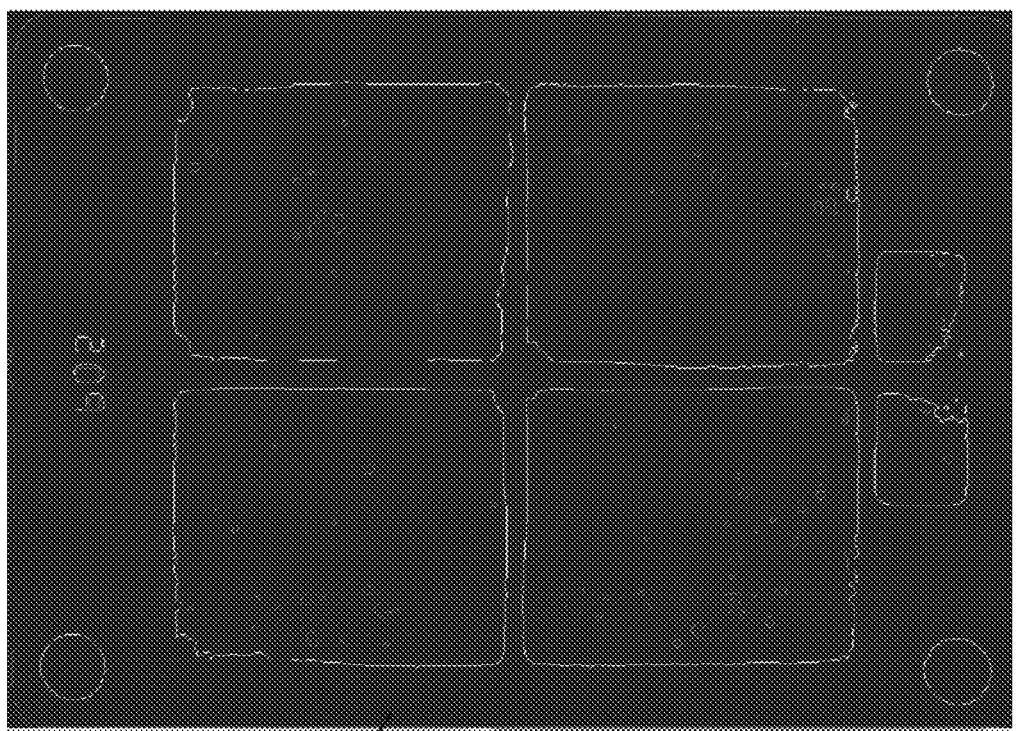
1400  Fig. 14
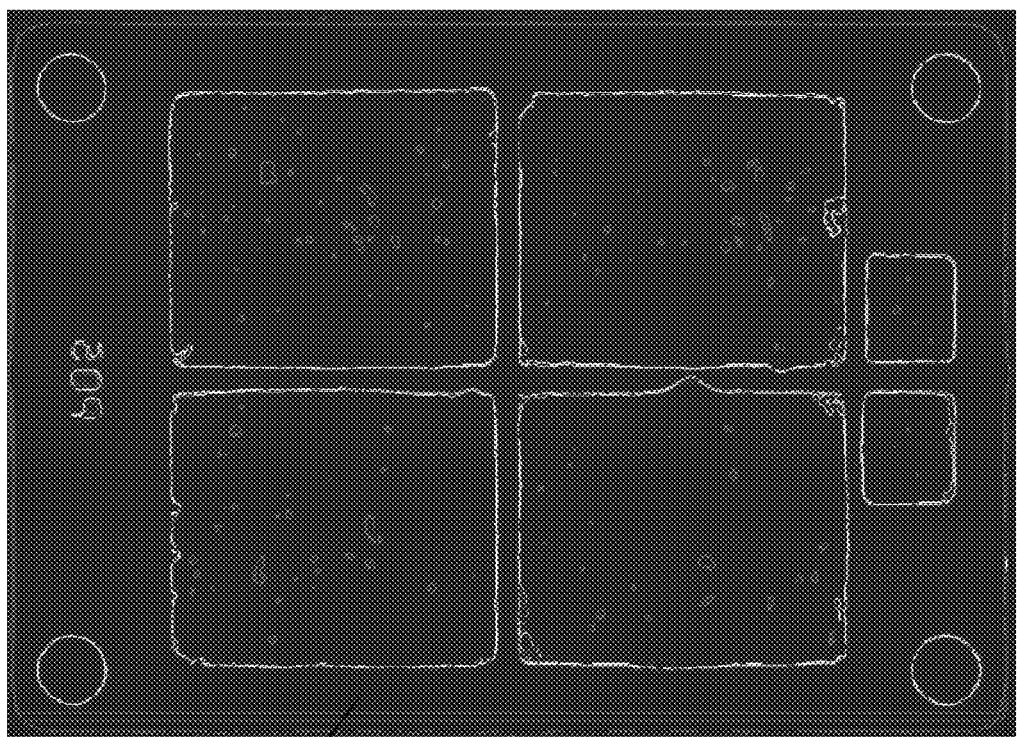
1500  Fig. 15

DELAMINATION TRACKING SYSTEMS AND METHODS

FIELD OF DISCLOSURE

The present disclosure relates to systems and methods for assessing and monitoring the delamination of a transistor or other circuit components.

BACKGROUND

One primary failure mode for some Propulsion Control Systems (PCS) is insulated-gate bipolar transistor (IGBT) failure, specifically delamination of the solder on the IGBT. When new generations of PCS have been deployed to the field for a number of years it is not apparent if IGBT failure due to delamination is still an issue. Some methods that have been used in an attempt to track IGBT failure due to delamination include performing a life test on the PCS using a nominal duty cycle seen by the Line Replaceable Units (LRU) and taking sonic images of the IGBTs every few months in an effort to determine how the IGBTs are handling the test. The images are typically reviewed visually, e.g., using an "eye ball test", or manually, e.g., by "tracing" a print out of the images or by digitally tracing the images using a graphical editing tool such as, e.g., MSPaint®. Each image is then compared to the other images to determine a baseline and the progress of delamination over time in an effort to measure expected life of the IGBT. However, such a manual process may be inaccurate as the reliance on human skill in tracing certain parts or portions of an image and measuring difference between the baseline and the image may not have a high degree of repeatable precision.

BRIEF SUMMARY

The disclosed analysis method and system may be used to automatically analyze images of a transistor to determine a percentage and progress of delamination in the transistor relative to a baseline image of the transistor.

In an aspect of the present disclosure, a method of determining delamination in a transistor is disclosed. The method includes loading a grey scale image of a transistor into memory, generating a black and white image based on the loaded grey scale image, identifying boundaries within the generated black and white image that have a size equal to or greater than a pre-determined size, cropping the black and white image based on the identified boundaries to generate a cropped black and white image, identifying at least one feature in the cropped black and white image based on the identified boundaries, normalizing the cropped black and white image based on an attribute of the identified at least one feature, cropping the grey scale image based on the normalized black and white image, comparing the cropped grey scale image to a baseline grey scale image of the transistor, and determining a change in a percentage of delamination of the transistor between the baseline grey scale image and the cropped grey scale image based on the comparison.

In some aspects, the method further includes generating a plot of the change in percentage of delamination, and presenting the plot to a user via a display.

In some aspects, generating the black and white image based on the loaded grey scale image includes generating a first black and white image by applying a first grey level threshold to the grey scale image and identifying boundaries within the generated black and white image includes identifying boundaries within the generated first black and white image. The method may further include determining that the number of identified boundaries for the first black and white image is greater than a pre-determined threshold number of boundaries, generating a second black and white image based on the loaded grey scale image by applying a second grey level threshold to the grey scale image, and identifying boundaries within the generated second black and white image that have at least the pre-determined size.

In some aspects, the second grey level threshold may be determined based on the Otsu Grey-Level Threshold technique.

In some aspects, cropping the black and white image based on the identified boundaries includes cropping the generated second black and white image based on the identified boundaries within the generated second black and white image.

In some aspects, the method further includes determining that the number of identified boundaries for the second black and white image generated by applying the second grey level threshold is greater than the pre-determined threshold number of boundaries, generating a third black and white image based on the loaded grey scale image by applying a third grey level threshold to the grey scale image, and identifying boundaries within the generated third black and white image that have at least the pre-determined size.

In some aspects, cropping the black and white image based on the identified boundaries includes cropping the generated third black and white image based on the identified boundaries within the generated third black and white image.

In some aspects, the third grey level threshold is greater than the first grey level threshold.

In some aspects, normalizing the cropped black and white image based on an attribute of the identified at least one feature includes calculating an area of the identified at least one feature and normalizing the cropped black and white image based on the calculated area.

In some aspects, the identified at least one feature is a screw hole.

In some aspects, determining the change in the percentage of delamination of the transistor between the baseline grey scale image and the cropped grey scale image based on the comparison includes calculating a first area of a substrate in the cropped grey scale image, the substrate corresponding to one of the identified boundaries, calculating a second area of a corresponding substrate in the baseline grey scale image, and determining based on the calculated first and second areas a percentage of delamination of the substrate in the cropped grey scale image relative to the corresponding substrate in the baseline grey scale image.

In an aspect of the present disclosure, a non-transitory computer readable medium is disclosed. The non-transitory computer readable medium includes instructions that, when executed by at least one processor including hardware, configure the at least one processor to load a grey scale image of a transistor into memory, generate a black and white image based on the loaded grey scale image, identify boundaries within the generated black and white image that have a size equal to or greater than a pre-determined size, crop the black and white image based on the identified boundaries to generate a cropped black and white image, identify at least one feature in the cropped black and white image based on the identified boundaries, normalize the cropped black and white image based on an attribute of the identified at least one feature, crop the grey scale image based on the normalized black and white image, compare the cropped grey scale image to a baseline grey scale image of the transistor; and determine a change in a percentage of delamination of the transistor between the baseline grey scale image and the cropped grey scale image based on the comparison.

In some aspects, instructions further configure the at least one processor to generate a plot of the change in percentage of delamination and present the plot to a user via a display.

In some aspects, generating the black and white image based on the loaded grey scale image includes generating a first black and white image by applying a first grey level threshold to the grey scale image and identifying boundaries within the generated black and white image includes identifying boundaries within the generated first black and white image where the instructions further configure the at least one processor to determine that the number of identified boundaries for the first black and white image generated by applying the first grey level threshold is greater than a pre-determined threshold number of boundaries, generate a second black and white image based on the loaded grey scale image by applying a second grey level threshold to the grey scale image, and identify boundaries within the generated second black and white image that have at least the pre-determined size.

In some aspects, the second grey level threshold is determined based on the Otsu Grey-Level Threshold technique.

In some aspects, the second grey level threshold is greater than the first grey level threshold.

In some aspects, cropping the black and white image based on the identified boundaries comprises cropping the generated second black and white image based on the identified boundaries within the generated second black and white image.

In some aspects, the instructions further configuring the at least one processor to determine that the number of identified boundaries for the second black and white image generated by applying the second grey level threshold is greater than the pre-determined threshold number of boundaries, generate a third black and white image based on the loaded grey scale image by applying a third grey level threshold to the grey scale image, and identify boundaries within the generated third black and white image that have at least the pre-determined size. In some aspects, cropping the black and white image based on the identified boundaries includes cropping the generated third black and white image based on the identified boundaries within the generated third black and white image.

In some aspects, the third grey level threshold is greater than the first and second grey level thresholds.

In some aspects, normalizing the cropped black and white image based on an attribute of the identified at least one feature includes calculating an area of the identified at least one feature and normalizing the cropped black and white image based on the calculated area.

In some aspects, the identified at least one feature is a screw hole.

In some aspects, determining the change in the percentage of delamination of the transistor between the baseline grey scale image and the cropped grey scale image based on the comparison includes calculating a first area of a substrate in the cropped grey scale image, the substrate corresponding to one of the identified boundaries calculating a second area of a corresponding substrate in the baseline grey scale image, and determining based on the calculated first and second areas a percentage of delamination of the substrate in the cropped grey scale image relative to the corresponding substrate in the baseline grey scale image.

In an aspect of the present disclosure, an apparatus is disclosed including at least one processor including hardware and memory. The memory stores instructions that, when executed by the at least one processor, configure the at least one processor to load a grey scale image of a transistor into memory, generate a black and white image based on the loaded grey scale image, identify boundaries within the generated black and white image that have a size equal to or greater than a pre-determined size, crop the black and white image based on the identified boundaries to generate a cropped black and white image, identify at least one feature in the cropped black and white image based on the identified boundaries, normalize the cropped black and white image based on an attribute of the identified at least one feature, crop the grey scale image based on the normalized black and white image, comparing the cropped grey scale image to a baseline grey scale image of the transistor, and determining a change in a percentage of delamination of the transistor between the baseline grey scale image and the cropped grey scale image based on the comparison.

In aspects of the present disclosure, apparatus, systems, and computer program products in accordance with the above aspects may also be provided. Any of the above aspects may be combined without departing from the scope of the present disclosure.

BRIEF DESCRIPTION OF THE DRAWINGS

The details of the present disclosure, both as to its structure and operation, can be understood by referring to the accompanying drawings, in which like reference numbers and designations refer to like elements.

FIG. 2A is a first C-mode Scanning Acoustic Microscopy (CSAM) grey scale image of a Powerex IGBT in accordance with some aspects of the present disclosure.

FIG. 2B is a second C-mode Scanning Acoustic Microscopy (CSAM) grey scale image of a Powerex IGBT in accordance with some aspects of the present disclosure, showing additional delamination of the Powerex IGBT as compared to the image of FIG. 2A.

FIG. 9 is an example of a cropped grey scale image in accordance with some aspects of the present disclosure.

FIG. 10 is an example of a composite image generated by overlaying a cropped grey scale image over a baseline grey scale image in accordance with some aspects of the present disclosure.

FIG. 14 is an example of a cropped individual grey scale image in accordance with some aspects of the present disclosure.

FIG. 15 is an example of a composite image generated by overlaying a cropped individual grey scale image over the baseline grey scale image in accordance with some aspects of the present disclosure.

DETAILED DESCRIPTION

The disclosed analysis method and system may be used to automatically analyze the images of transistors and other circuit components including substrates and attached dies to determine a percentage and progress of delamination in the transistor relative to a baseline image of the transistor.

While described below with reference insulated-gate bipolar transistors (IGBTs), in some aspects, for example, the method and system may be used to analyze any other transistor or other circuit component including metal-oxide-semiconductor field-effect transistors (MOSFETs), silicon carbide MOSFETs, Gallium Nitride field effect transistors (GaN FETs), bipolar junction transistors (BjTs) or any other transistors or circuit components including substrates and attached dies.

In some aspects, the system may implement or execute software that takes a series of images of an IGBT and compares each image to an initial baseline. The comparison may include computing a graph and a percent delamination of each image relative to the baseline to determine a progress of the delamination over the series of images. In some aspects, an Otsu Grey-Level Threshold technique may be used to create black and white images with some additional logic as described below and a "Zero-cross Method of Edge Detection with Closed Contours" technique may be used to segregate each substrate, screw, etc. from the black and white images. The system may also automatically perform adjustments to the various images to account for various issues such as, e.g., different image sizes, intensities, and orientations between each image. The system may generate an output chart, plot, or graph that is similar to the typical life curve representation for an IGBT commonly printed on datasheets. This allows a user reviewing life curves of IGBTs to determine how much a IGBTs life has been reduced due to delamination.

Figure 1:
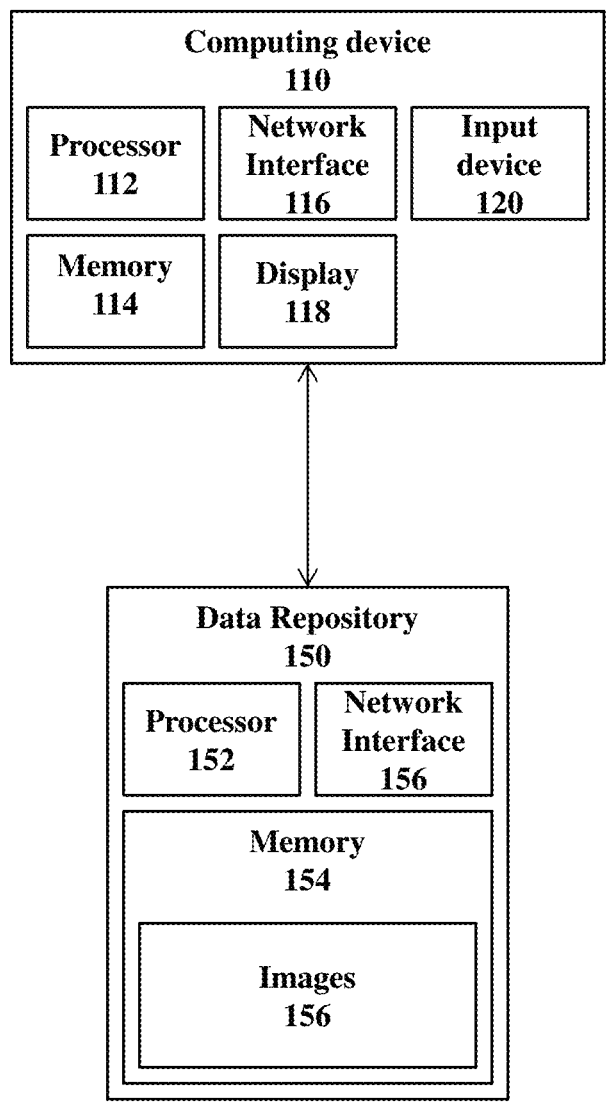
FIG. 1 is a system diagram illustrating a system for determining delamination in a transistor in accordance with some aspects of the present disclosure.

With reference now to FIG. 1, a system 100 for tracking delamination in an IGBT is illustrated. In some aspects, system 100 includes a computing device 110, and a data repository 150.

Computing device 110 includes at least one processor 112, memory 114, at least one network interface 116, a display 118, an input device 120, and may include any other features commonly found in a computing device. In some aspects, computing device 110 may, for example, be a computing device that is configured to present a user with data related to the delamination of IGBTs. In some aspects, computing device 110 may include, for example, a personal computer, laptop, tablet, smart device, smart phone, smart watch, or any other similar computing device.

Processor 112 may include, for example, a microcontroller, Field Programmable Gate Array (FPGAs), Application Specific Integrated Circuit (ASIC), programmable array logic (PAL), programmable logic array (PLA), or any other processor that is configured to perform various operations. Processor 112 may be configured to execute instructions as described below. These instructions may be stored, for example, in memory 114. As used herein, the term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually.

Memory 114 may include, for example, non-transitory computer readable media in the form of volatile memory, such as random access memory (RAM) and/or cache memory or others. Memory 114 may include, for example, other removable/non-removable, volatile/non-volatile storage media. By way of non-limiting examples only, memory 114 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 116 is configured to transmit and receive data or information to and from data repository 150 or any other computing device via wired or wireless connections. For example, network interface 116 may utilize wireless technologies and communication protocols such as Bluetooth®, WIFI (e.g., 802.11a/b/g/n), cellular networks (e.g., CDMA, GSM, M2M, and 3G/4G/4G LTE), near-field communications systems, satellite communications, via a local area network (LAN), via a wide area network (WAN), or any other form of communication that allows computing device 110 to transmit or receive information to or from data repository 150.

Display 118 may include any display device that is configured to display information to a user of computing device 110. For example, in some aspects, display 118 may include a computer monitor, television, smart television, or other similar displays. In some aspects, display 118 may be integrated into or associated with computing device 110, for example, as a display of a laptop, smart phone, smart watch, or other smart wearable devices, as a virtual reality headset associated with computing device 110, or any other mechanism for displaying information to a user. In some aspects, display 118 may include, for example, a liquid crystal display (LCD), an e-paper/e-ink display, an organic LED (OLED) display, or other similar display technologies. In some aspects, display 118 may be touch-sensitive and may also function as an input device 120.

Input device 120 may include, for example, a keyboard, a mouse, a touch-sensitive display 118, a keypad, a microphone, or other similar input devices or any other input devices that may be used alone or together to provide a user with the capability to interact with computing device 110.

Data repository 150 includes a processor 152, memory 154, and a network interface 156 that may include similar functionality as processor 112, memory 114, and network interface 116. In some aspects, data repository 150 may, for example, be any computing device, server, database, or similar system that is configured to interact with or provide data to computing device 110. For example, in some aspects data repository 150 may store one or more IGBT images 156 in memory 154 that may be retrieved by computing device 110 for further analysis. In some aspects, IGBT images 156 may alternatively be stored directly in memory 114 of computing device 110. In some aspects, the IGBT images 156 stored in memory 154 may be generated using C-mode Scanning Acoustic Microscopy (CSAM) on the IGBT. These CSAM images show the inside of an object at a given cross section. By comparing these IGBT images 156, the same cross section of the IGBT may be assessed for delamination.

With reference now to FIGS. 2A, 2B, 3A, and 3B, grey scale images of a Powerex IGBT 200 and Fuji IGBT 300 are illustrated with dies in various states of delamination. For example, as illustrated in FIGS. 2A and 2B, IGBT 200 includes a first die 202 and a second die 204. As can be seen from FIG. 2A, for example, a delamination region 206 of first die 202 is present, e.g., near a corner of the first die 202. A delamination region 208 of second die 204 is also present in FIG. 2A. With reference to FIGS. 2A and 2B, the progression of delamination in IGBT 200 is illustrated. For example, as seen in FIG. 2B, delamination region 206 has expanded from the corner and now reaches to two other corners of the first die 202. Likewise, delamination region 208 has expanded to a much larger portion of second die 204.

Figure 3A:
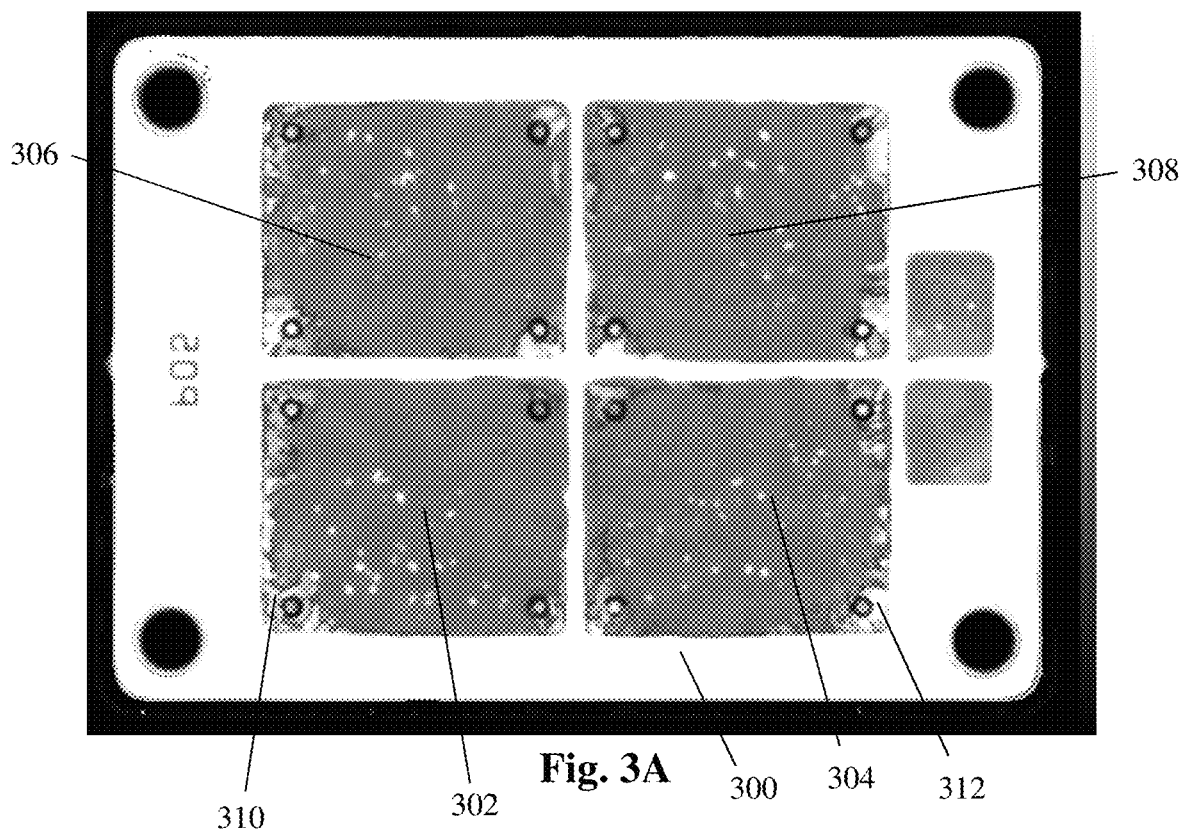
FIG. 3A is a first C-mode Scanning Acoustic Microscopy (CSAM) grey scale image of a Fuji IGBT in accordance with some aspects of the present disclosure.
Figure 3B:
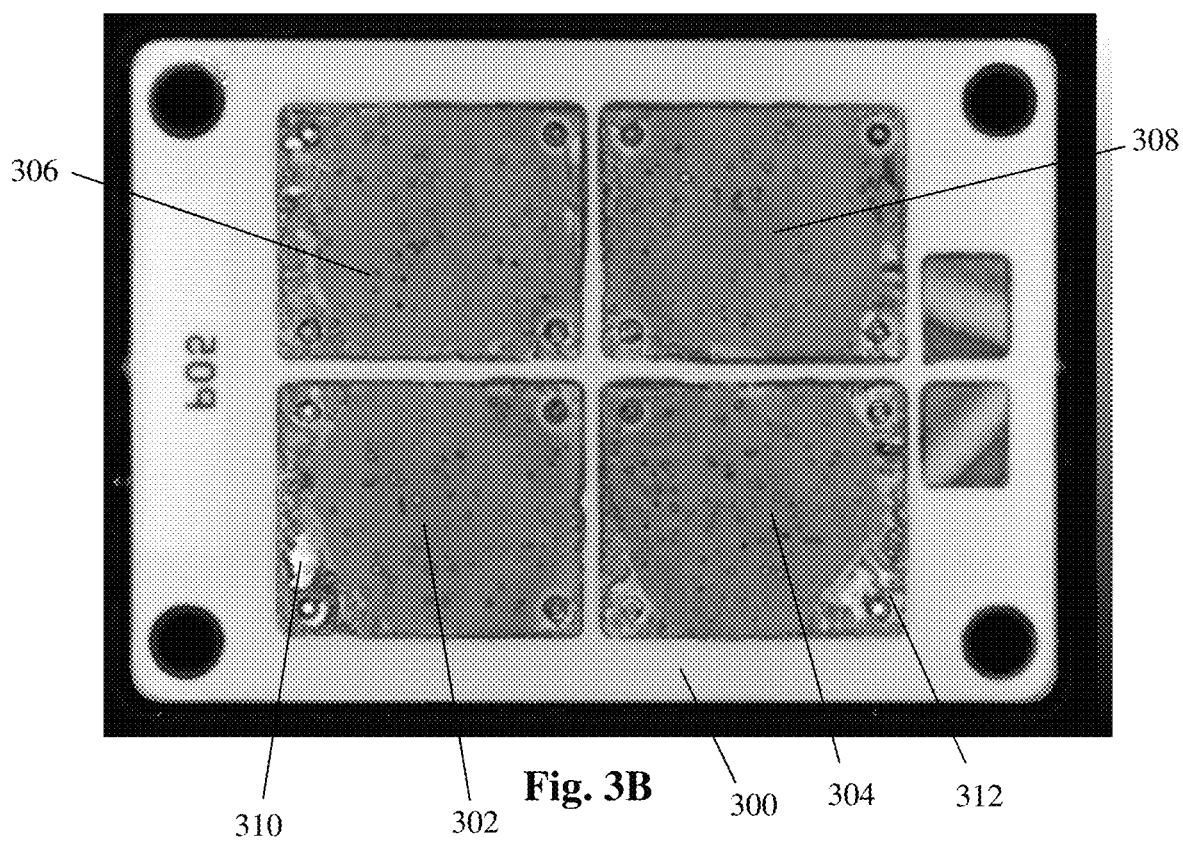
FIG. 3B is a second C-mode Scanning Acoustic Microscopy (CSAM) grey scale image of a Fuji IGBT in accordance with some aspects of the present disclosure, showing additional delamination of the IGBT as compared to the image of FIG. 3A.

With reference now to FIGS. 3A and 3B, IGBT 300 includes a first die 302 and a second die 304, a third die 306, and a fourth die 308. As can be seen from FIG. 3A, for example, a delamination region 310 of first die 302 is present, e.g., near a bottom left corner of the first die 302. A delamination region 312 of second die 304 is also present in FIG. 3A, e.g., near a bottom right corner of second die 304. Dies 306 and 308 also include delamination regions. With reference to FIGS. 3A and 3B, the progression of delamination in IGBT 300 is illustrated. For example, as seen in FIG. 3B, delamination region 310 has expanded from the bottom left corner and now reaches toward the top left corner of the first die 302. Likewise, delamination region 312 has expanded from the bottom right corner and now extends toward the top right corner and part of the way toward a center of the second die 304.

The delamination seen in FIGS. 2A, 2B, 3A, and 3B for IGBTs 200 and 300 may occur over time, for example, due to repeated use cycles of the IGBTs. For example, high temperatures or high current densities may cause delamination over time as the IGBTs age, e.g., due to expansion and contraction of the dies causing separation. The delamination of the IGBTs over time may lead to failure of the IGBTs. Because of this, data generated by tracking and analyzing IGBT delamination may be utilized as an important factor in predicting future IGBT failures or in determining whether an IGBT needs to be replaced or serviced.

Figure 4:
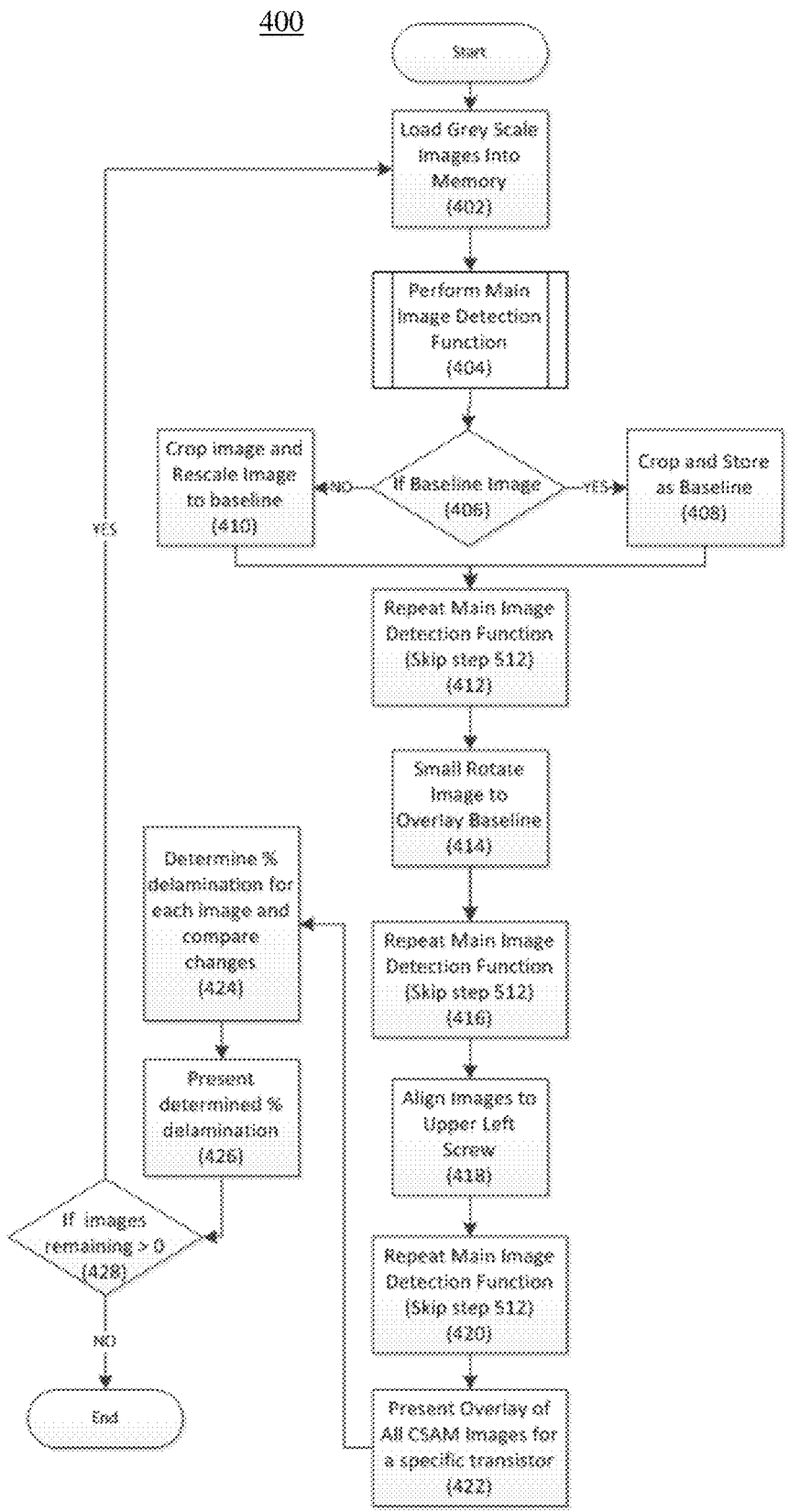
FIG. 4 is a flow chart of a method of determining delamination in a transistor in accordance with some aspects of the present disclosure.

With reference now to FIG. 4, a method 400 for computer automated analysis and tracking of the delamination of an IGBT such as, e.g., IGBT 200, in a plurality of successive images is illustrated.

At 402, computing device 110 loads grey scale images of an IGBT into memory 114. For example, the grey scale images may be a plurality of successive CSAM images of the IGBT taken over a period of time such as, e.g., days, months, years, etc. In some aspects, for example, the grey scale images may be retrieved from data repository 150 or another source by computing device 110. For example, gray scale images of the IGBT may be loaded based on a file name or folder structure in memory 114 of computing device 110, memory 154 of data repository 150, or any other source. In some aspects, for example, with reference to FIGS. 2A and 2B, a grey scale image of IGBT 200, e.g., a PowerEx® CM600DY-24A IGBT sold by Powerex Inc., may be loaded into memory 114 including dies 202 and 204. In some aspects, for example, with reference to FIGS. 3A and 3B, a grey scale image of a second IGBT, e.g., a Fuji 2MBI600VE_120_50 IGBT sold by Fuji Electric Co. Ltd., may alternatively be loaded into memory 114 including dies 302 and 304. While the PowerEx and Fuji IGBTs are presented as examples, grey scale images for any IGBT may be loaded into memory without departing from the scope of the present disclosure.

At 404, a main image detection function is performed on each loaded image. One example of a main image detection function 500 is shown in FIG. 5.

Figure 5:
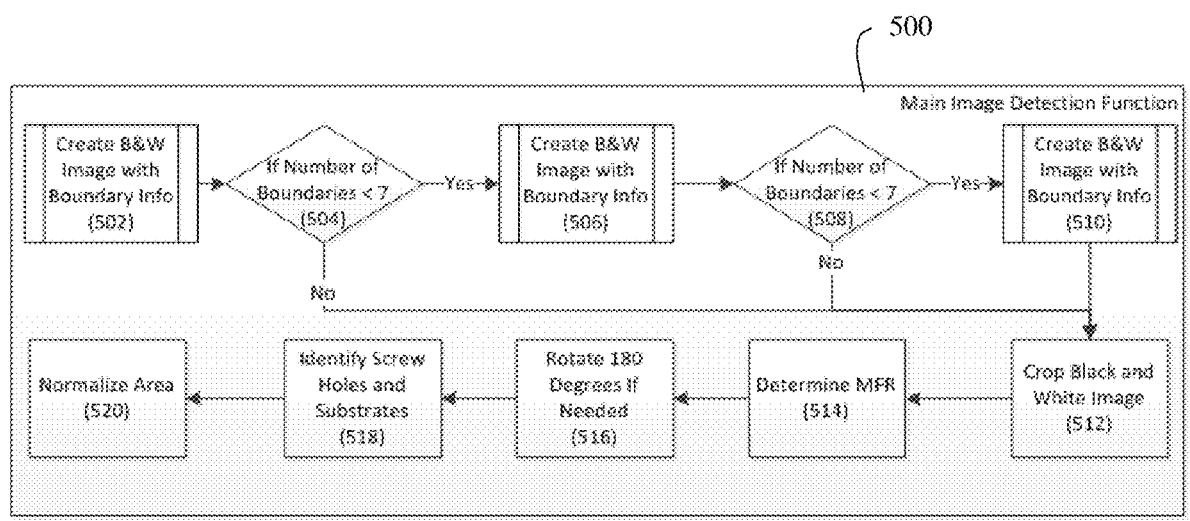
FIG. 5 is a flow chart of a main image detection function of the method of FIG. 4 in accordance with some aspects of the present disclosure.

As shown in FIG. 5, at 502, a first black and white image is created based on the loaded image being processed and boundary information is generated for the first black and white image. For step 502, the first black and white image is generated using a first grey level threshold. In some aspects, the first grey level threshold may have a pre-determined value. For example, the first grey level threshold may be a grey level threshold of 25%. In some aspects, the first grey level threshold may be a value in the range of about 20% to about 30%. In some aspects, any other value for the first grey level threshold may be used. In some aspects, the first grey level threshold may be modifiable by a user of computing device 110.

Figure 6:
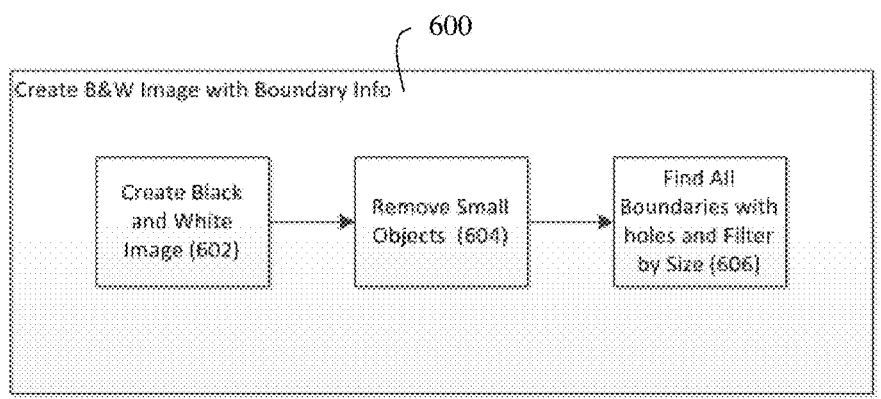
FIG. 6 is a flow chart of a sub-method of the main image detection function of FIG. 5 for creating black and white images in accordance with some aspects of the present disclosure.

One example of step 502 is a method 600 shown in FIG. 6. As shown in FIG. 6, at 602, the black and white image is created, for example, based on the grey level threshold specified by main image detection function 500 for the corresponding step, e.g., values above the grey level threshold may be set as white while values below the grey level threshold may be set as black or vice versa. For step 502, for example, the first black and white image may be created based on the first grey level threshold, e.g., a 25% grey level threshold.

At 604, any small objects in the created first black and white image are removed. For example, any objects having a size less than a pre-determined number of pixels, e.g., five pixels, 10 pixels, or any other number of pixels that is configured to remove objects that are not significant to the analysis, and having a predefined number of connected neighbors, e.g., four connected neighbors, six connected neighbors, eight connected neighbors, or any other number of connected neighbors, may be removed from the image. In some aspects, the pre-determined number of pixels may be set at a value that is configured to remove any anomalies within an image, e.g., anomalies generated during capture of the image by the camera.

Figure 7:
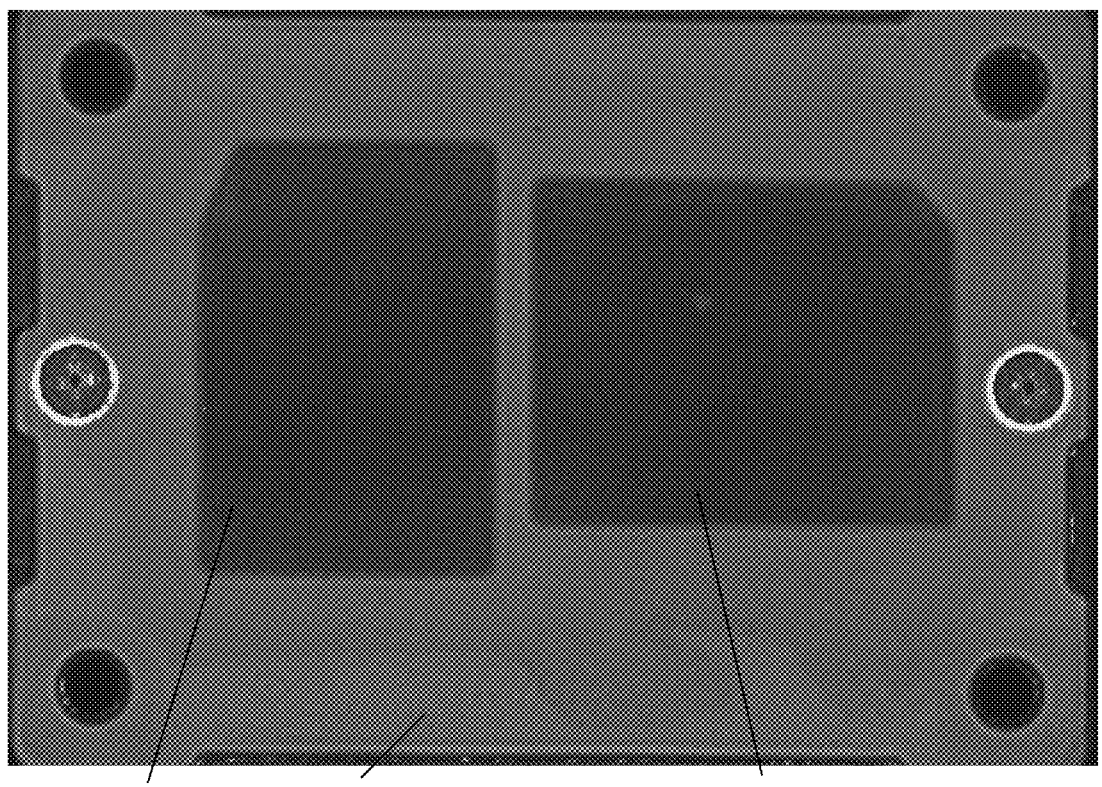
FIG. 7 is an example of a black and white image generated from a CSAM grey scale image of a Powerex IGBT in accordance with some aspects of the present disclosure.
Figure 12:
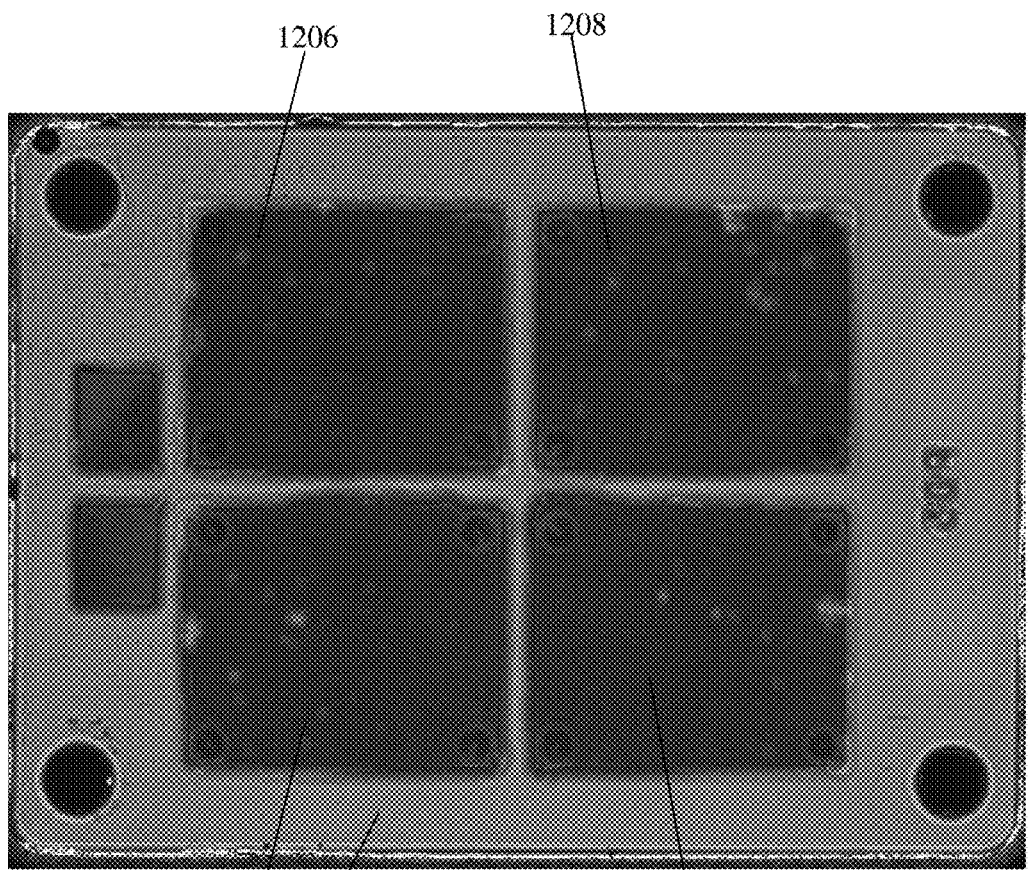
FIG. 12 is an example of a black and white image generated from a CSAM grey scale image of a Fuji IGBT in accordance with some aspects of the present disclosure.

Example black and white images created during steps 602 and 604 are illustrated in FIGS. 7 and 12. For example, FIG. 7 illustrates a black and white image 700 of Powerex® IGBT including dies 702 and 704 while FIG. 12 illustrates an example of a black and white image 1200 of a Fuji IGBT including dies 1202, 1204, 1206, and 1208.

At 606, all boundaries with holes may be found and filtered by size. For example, boundaries may be filtered according to the following equation:

$$\text{Boundaries area} > (\text{Image} \times \text{Length} \times \text{image factor})^2 \quad (1)$$

Where Image×Length is a length of the image, e.g., number of pixels, in a horizontal direction, e.g., as seen in FIG. 7, and the image factor is a value tuned to determine the minimum area of a boundary to be considered significant relative to the overall image size (as defined by Image× Length). In some aspects, for example, an image factor value of 0.053 may be used. In some aspects, the image factor may be any other value depending on the particular application, resolution, camera used, image size, or any other considerations that may be used to identify objects that may be significant to the analysis.

Figure 8:
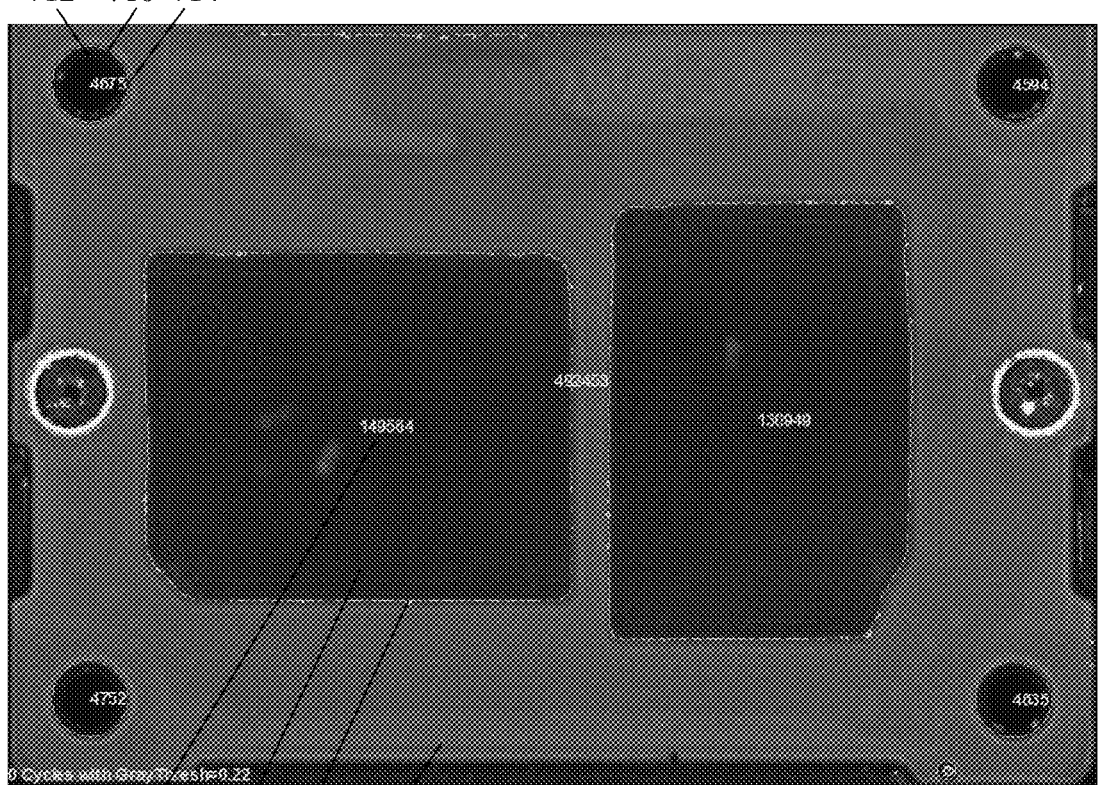
FIG. 8 is an example of a black and white image including identified boundaries in accordance with some aspects of the present disclosure.

As illustrated in FIG. 8, all boundaries are identified for the image 700, e.g., as boundary lines or indicators around each object in the image. In some aspects, computing device 110 may present image 700 to the user, e.g., via display 118, including the identified boundaries highlighted with at least one indicator, e.g., a highlight, colored line, etc. For example, a boundary of die 702 may be illustrated with a boundary line or other indicator 706 as shown, for example, in FIG. 8.

Figure 13:
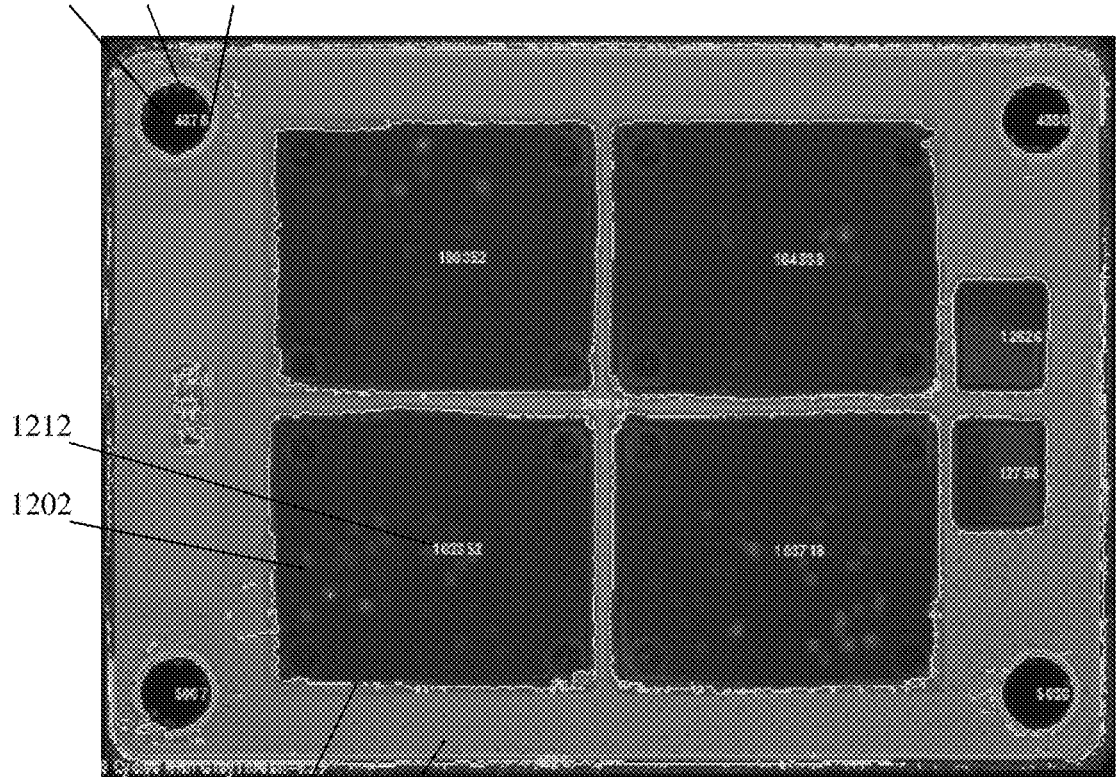
FIG. 13 is an example of a black and white image including identified boundaries in accordance with some aspects of the present disclosure.

As another example, as illustrated in FIG. 13, all boundaries are identified for the image 1200, e.g., as boundary lines or indicators around each object in the image. In some aspects, computing device 110 may present image 1200 to the user, e.g., via display 118, including the identified boundaries highlighted with at least one indicator, e.g., a highlight, colored line, etc. For example, a boundary of die 1202 may be illustrated with a boundary line or other indicator 1210 as shown, for example, in FIG. 13. In some aspects, there is no need to present a user with an image that shows the identified boundaries.

With reference again to FIG. 5, once the first black and white image has been created and boundary information generated, the number of boundaries found in step 606 is compared to a pre-determined threshold number of boundaries at 504. For example, if the number of detected boundaries in the first black and white image is less than the pre-determined threshold number of boundaries, for example, seven boundaries, further processing by method 600 may be performed at 506. For example, IGBTs may have at least eight boundaries of interest, e.g., screw holes, substrates/dies, or other similar features. For example, as illustrated in FIG. 8, image 700 includes six screw holes and two substrates/dies, e.g., eight boundaries. If the number of detected boundaries in the first black and white image is greater than or equal to the pre-determined threshold number of boundaries, the method instead proceeds to step 512. In some aspects, for example, while there may be eight boundaries of interest, the pre-determined threshold number of boundaries may be set to a lower number of boundaries, e.g., to seven, six, or fewer boundaries, to account for boundary discrepancies in images where, for example, a screw hole or other boundary of interest may fail to be recognized or detected in the image. For example, as illustrated in FIG. 8 the internal packaging holes on each side of the IGBT were not detected in the image as a boundary (e.g., no area was calculated and no border generated). Accordingly, only four screw holes, two dies, and the boundary of the IGBT itself were detected, a total of seven boundaries. Setting the pre-determined threshold number of boundaries to a value less than the number of boundaries of interest allows boundary information to be generated for the IGBT even when some features of interest in the IGBT are not detected.

At 506, a second black and white image is created based on the loaded image that is being processed and boundary information is generated for the third black and white image according to method 600 of FIG. 6. For step 506, the black and white image is generated using a second grey level threshold. In some aspects, the second grey level threshold may be determined using the Otsu Grey-Level Threshold technique. For example, the second grey level threshold may be determined to be a grey level threshold of in the range from 0% to 100% based on the particular characteristics of the image being processed using the Otsu Grey-Level Threshold technique. Method 600 is then performed based on the second grey level threshold.

Once the second black and white image has been created based on the second grey level threshold and boundary information has been generated according to method 600, the number of boundaries found in step 606 for the second black and white image is compared to a pre-determined threshold number of boundaries at 508. For example, if the number of detected boundaries in the second black and white image is less than the pre-determined threshold number of boundaries, for example, seven boundaries, further processing by method 600 may be performed at 510. If the number of detected boundaries in the second black and white image is greater than or equal to the pre-determined threshold number of boundaries, the method instead proceeds to step 512.

At 510, a third black and white image is created based on the loaded image that is being processed and boundary information is generated for the third black and white image according to method 600 of FIG. 6. For step 510, the third black and white image is generated using a third grey level threshold. In some aspects, the third grey level threshold may have a pre-determined value. For example, the third grey level threshold may be a grey level threshold of 80%. In some aspects, the third grey level threshold may be a value in the range of about 75% to about 85%. In some aspects, any other value for the third grey level threshold may be used. In some aspects, the third grey level threshold may be modifiable by a user of computing device 110. Method 600 is then performed based on the third grey level threshold and the main image detection function 500 proceeds to 512.

By comparing the number of detected boundaries in the generated black and white image to the pre-determined threshold number of boundaries, the grey level threshold to be used in the image may be optimized. For example, if the image generated using the first grey level threshold includes a sufficient number of detected boundaries to meet the pre-determined threshold number of boundaries, the image generated using the first grey level threshold is used. Otherwise, a black and white image generated using the second grey level threshold will be tested. If the image generated using second grey level threshold includes a sufficient number of detected boundaries to meet the pre-determined threshold number of boundaries, the image generated using the second grey level threshold is used. Otherwise, an image generated using the third grey level threshold will be used. In some aspects, for example, the first and third grey level thresholds may be used as upper and lower limits on the output of the Otsu Grey-Level Threshold technique, for example, if this technique is used to generate the second grey level thresholds.

At 512, the first, second, or third black and white image, depending on whether the pre-determined number of boundaries was met in either 504 or 508, is cropped to remove features other than the IGBT. For the remainder of the steps the first, second, or third black and white image will be referenced generically as "the black and white image". For example, as illustrated in FIGS. 9 and 14, the images 700 and 1200 have been cropped at the border of the IGBT such that only the features within the IGBT itself remain. For example, in the image, the IGBT will have the largest boundary by area. Therefore, to determine which boundary corresponds to the border of the IGBT, the generated boundary information may be analyzed to determine which boundary is the largest boundary by area. Once identified, the image may be cropped to the determined largest boundary. For example, the image features within the borders of the IGBT boundary remain while any other features in the image outside of the border of the IGBT are cropped out, such as, e.g., the color bar labeled as 210 in FIG. 2. Borders of other objects including, for example, screw holes, other dies, and similar features may also be retained since they are within the border of the IGBT. In some aspects, the cropping may be performed based on a smallest fit rectangle or other geometric shape that includes the boundary of the IGBT.

In some aspects, the "Zero-cross Method of Edge Detection with Closed Contours" technique may also be used to segregate each substrate, screw, etc., from the black and white images. For example, the "Zero-cross Method of Edge Detection with Closed Contours" technique may be used to verify the results of steps 504-512.

At 514, the manufacturer (MFR) of the IGBT is determined for the black and white image. In some aspects, for example, the MFR may be determined based on 2 or 4 main substrates of the IGBT. For example, if there are 2 main substrates, the MFR may be determined to be Powerex IGBT. In another example, if there are 4 main substrates, the MFR may be determined to be Fuji IGBT. In another example, the MFR may be determined based on the locations of the substrates, screws, or any other feature of the IGBT. For example, if two substrates are located on or mostly on one side of the IGBT relative to a centroid of the IGBT, the IGBT may be determined to be a Fuji IGBT.

At 516, the orientation of the black and white image may be determined, for example, based on the position or orientation of the boundaries, the position of any holes in the IGBT, or other similar features. For example, the position of holes in the IGBT may be analyzed to determine whether the IGBT is oriented in a first orientation or a second orientation. As an example, the first orientation may be the orientation illustrated in FIG. 7 or 12 while a second orientation may be any other orientation including, for example, an orientation rotated 90, 180 or any other number of degrees from the first orientation. In some aspects, each image that is processed into black and white during the main image detection function 500 may need to be oriented or re-orientated into a common orientation for comparison. For example, the first orientation may be defined as the orientation to be used for comparison and any black and white images that are not oriented in the first orientation may need to be rotated to match the first orientation. For example, a black and white image having an orientation that is 180 degrees from the first orientation (e.g., upside-down relative to an image in the first orientation) may need to be rotated 180 degrees to match the first orientation. Matching the orientations of the images allows the same features in each image to later be compared by the computing device. For example, the same die, e.g., die 702 of FIG. 7, illustrated in each successive image may be compared in the same orientation so that the progress of delamination in die 702 may be determined for a particular IGBT.

At 518, screw holes and substrates in the black and white image are identified. For example, the objects in the black and white image may be compared to a threshold size to determine whether they are screw holes. For example, if a screw hole is known to be a pre-determined number of pixels in diameter or to be within a pre-determined area of pixels, e.g., 5×5 area of pixels, image processing may be used to determine whether any objects fit within the pre-determined diameter or area and those objects may be identified as screw holes. Likewise, the centroid of the black and white image may be used to identify the substrates.

In some aspects, for example, each group of white pixels in the black and white image may be sorted by size. For example, each group of white pixels may be sorted by size and identified in an array or other data structure. The data structure may include, for example, the number of pixels within the borders of the group and X and Y coordinate data for the group, e.g., at the center of the group. Since each image is scaled to the same size and cropped, the size of each type of object in pixels or area may already be known. The substrates may then be identified by accessing the array for the groups that have the largest size, e.g., number of pixels, aside from the IGBT itself. The centroid of each substrate may then be used to orient and determine a location of the substrate relative to the IGBT. For example, the array may include coordinates for each group that may be used to locate the centroid and determine the location of each object. These determinations may allow the same substrate in different images of the IGBT to be later compared against each other.

Once the substrates have been identified, the next largest groups in the array will be the screw holes and internal packaging holes in the center. The locations of the screw holes and internal packaging holes may be determined based on the coordinate data stored in the array.

With reference to FIGS. 8 and 13, for example, each detected boundary may define an area. For example, as illustrated in FIG. 8, a boundary 706 of die 702 may include an area 708 of 149564. In some aspects, this area may be represented in pixels. With further reference to FIG. 8, a first screw hole 710 may include a boundary 712 and an area 714 of 4675 pixels. As another example, as illustrated in FIG. 13, a boundary 1210 of die 1202 may include an area 1212 of 102352. In some aspects, this area may be represented in pixels. With further reference to FIG. 13, a first screw hole 1214 may include a boundary 1216 and an area 1218 of 4675 pixels At 520, the area of the black and white image is normalized such that the features of the image are rescaled to a pre-determined size, e.g., a size of the corresponding features found in a baseline image. For example, the image may be normalized based on the size of the screw holes in the image. For example, the screw hole 708 of image 700 may have a known size that does not change during use of the IGBT. Since the size does not change, the size of the screw holes may be used as a reference for normalization. For example, a target image normalization may be an image having screw holes that are a pre-determined number of pixels in diameter or have a predetermined area. For example, the generated black and white images may be normalized at 520 such that the screw holes have a pre-determined area in pixels, a pre-determined diameter, or some other similar measure. For example, image 700 may be normalized, e.g., rescaled or otherwise adjusted, such that the boundary area 712 of 4675 pixels for screw hole 708 becomes 5000 pixels. Using the area, diameter, or other measurements of the screw holes as a reference allows each image to be scaled or normalized to the same size since the dimensions of each particular screw hole does not vary with additional usage of the IGBT.

In some aspects, the image may also or alternatively be normalized based on a distance between each screw. For example, a distance between a first screw and a second screw in an IGBT image may be used as a basis for normalization. For example, a distance between the top left and top right screws as shown in FIG. 8 may be used to normalize the image.

With reference again to FIG. 4, once main image detection function 500 has been performed, computing device 110 determines whether the grey scale image is a baseline image at 406. For example, if the grey scale image is the first image generated for this IGBT computing device 110 may determine that this image is the baseline image. For example, computing device 110 may search memory 114 or data repository 150 to determine whether any other images for this IGBT have been previously processed using method 400. In some aspects, computing device 110 may determine whether the image is a baseline image based on the filename, date, or any other criteria. FIGS. 7 and 12 are examples of baseline images. In some aspects, the baseline image may not be an image of the same IGBT as successive images. For example, for a particular model number, a generic baseline image may be used against which some or all of the other IGBTs having that model number may be compared.

In some aspects, the user may specify whether an image is a baseline image. For example, the user may input an indication, e.g., using input device 120, that a particular CSAM grey scale image will be used to generate a grey scale baseline image. In some aspects, the user may input an indication, e.g., using input device 120, that the grey scale image is a baseline image at 406. In some aspects, the computing device 110 may determine that the image is a baseline image based on the user's input.

At 408, if computing device 110 determines that the grey scale image is a baseline image, the grey scale image may crop the grey scale image based on the cropping performed on the black and white image and may store the cropped grey scale image as a baseline image, e.g., in memory 114 or data repository 150.

At 410, if computing device 110 alternatively determines that the grey scale image is not a baseline image, the grey scale image may be cropped based on the cropping performed on the black and white image at 512 and may be rescaled to match the scale of the baseline image using the boundary and other information generated for the black and white image during main image detection function 500. For example, the grey scale image may be rescaled based on the comparison of a feature of the grey scale image such as, e.g., a screw hole, to the same feature, e.g., a corresponding screw hole, found in the baseline image. The grey scale image may then be rescaled such that the size of the feature in the grey scale image matches the size of the corresponding feature in the baseline. In some aspects, for example, the size of the feature may be determined based on the boundary information for the corresponding black and white image. In some aspects, for example, the grey scale image may be rescaled based on the distance between the upper left and upper right screw holes. Examples of individual cropped and rescaled grey scale images 900 and 1400 for each of the Powerex and Fuji IGBTs, respectively, are illustrated in FIGS. 9 and 14.

At 412, computing device 110 may repeat the main image detection function 500 on the cropped and rescaled grey scale image with the exception that step 512 of the main image detection function 500 may be skipped. The main image detection function 500 may be repeated because the image has now changed due to cropping, rescaling, or both. For example, the main image detection function 500 may be more effective with the grey scale image cropped to remove the empty space and color bar from the CSAM image. In some aspects, step 412 may be skipped.

At 414, if the grey scale image is not the baseline image, the grey scale image may be further adjusted or rotated to overlay the baseline. For example, if the grey scale image is offset rotationally relative to the baseline image, e.g., by a small number of degrees such as 5 or 10 degrees, a small rotation of the grey scale image may be used to match the rotation of the grey scale image to the baseline.

At 416, computing device 110 may repeat the main image detection function 500 on the rotated grey scale image with the exception that step 512 of the main image detection function 500 may be skipped. The main image detection function 500 may be repeated because the image has now changed due to the small rotation. In some aspects, step 416 may be skipped.

At 418, the cropped, rescaled, and rotated grey scale image may be aligned to a feature of the baseline grey scale image, e.g., the upper left screw, substrates, or any other feature having an identified boundary from main image detection function 500.

At 420, computing device 110 may repeat the main image detection function 500 on the cropped and rescaled grey scale image with the exception that step 512 of the main image detection function 500 may be skipped. The main image detection function 500 may be repeated because the image has now changed due to the alignment of the grey scale image with the baseline. In some aspects, step 420 may be skipped.

At 422, an overlay for all of the images for the IGBT is generated. For example, as illustrated in FIG. 10, once normalized, the successive cropped, rescaled, rotated, and aligned grey scale images for the Powerex IGBT may be overlaid to generate a composite image 1000 that shows the progress of the delamination. In some aspects, the composite image 1000 may be presented to the user, e.g., via display 118. In some aspects, for example, each overlaid image may include boundaries having a different color. For example, the baseline may have white boundaries, a first subsequent image may have red boundaries, a second subsequent image may have blue boundaries, etc. This difference in color may allow the user to visually inspect the presented composite image 1000 and recognize the progress of the delamination of the IGBT. In some aspects, the generation of a composite image 1000 may be skipped and no generated composite image 1000 may be presented to the user.

As another example, as illustrated in FIG. 15, once normalized, the successive cropped, rescaled, rotated, and aligned images for the Fuji IGBT may be overlaid to generate a composite image 1500 that shows the progress of the delamination. In some aspects, the composite image 1500 may be presented to the user, e.g., via display 118. In some aspects, the generation of a composite image 1500 may be skipped and no generated composite image 1500 may be presented to the user.

At 424, a percentage of delamination relative to the baseline for each grey scale image may be determined by calculating delamination for each image and substrate size. For example, after normalization, the delamination may be calculated using the equation (2) below, where n_i is the number of pixels in the area of a substrate at i number of cycles when normalized and where n_b is the number of pixels in the area of the same substrate in the a baseline image.

$$\text{Delamination Percentage} = n\_i/n\_b \quad (2)$$

Figure 11:
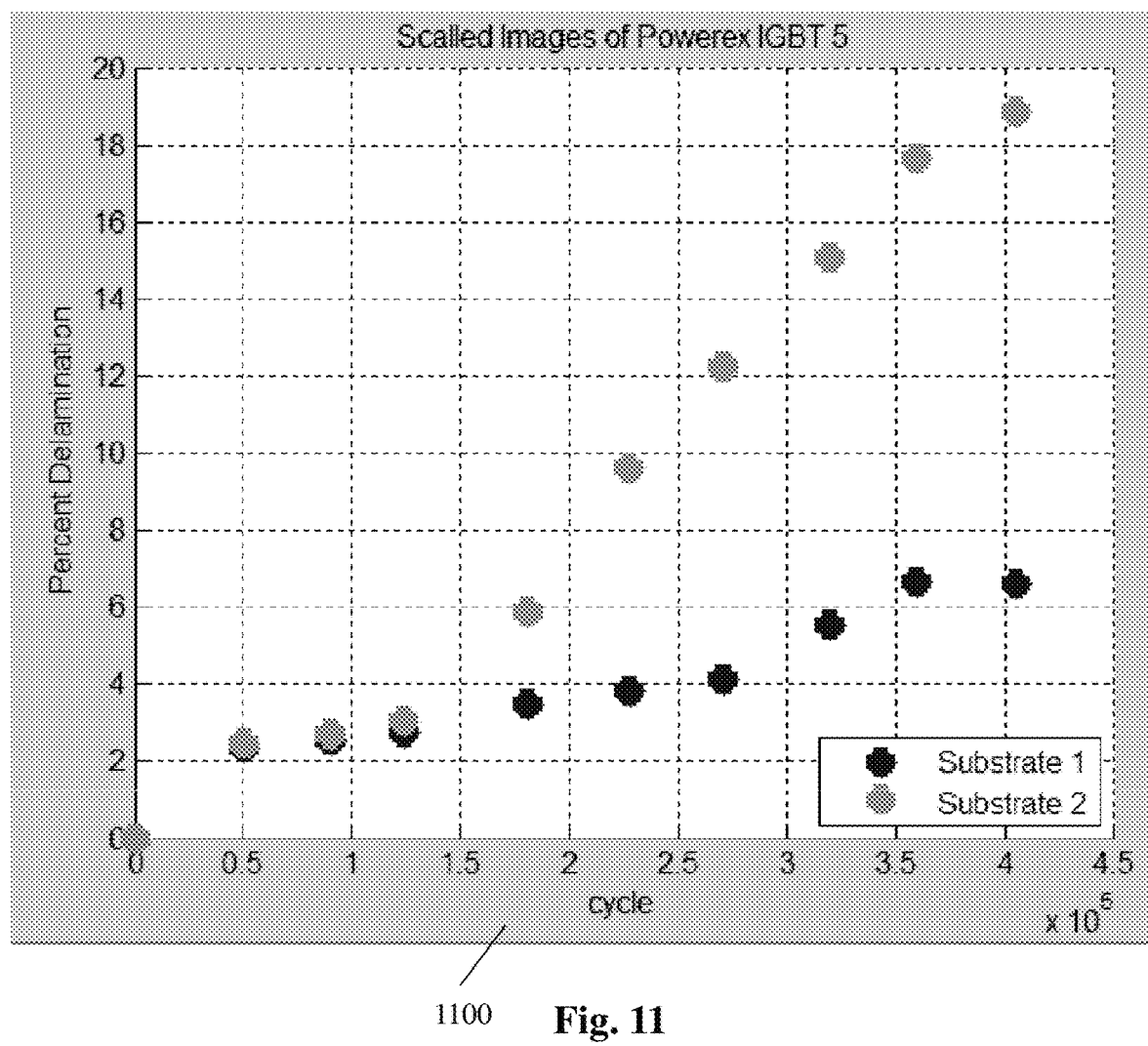
FIG. 11 is a plot of the percentage of delamination vs. number of cycles for a Powerex IGBT in accordance with some aspects of the present disclosure.
Figure 16:
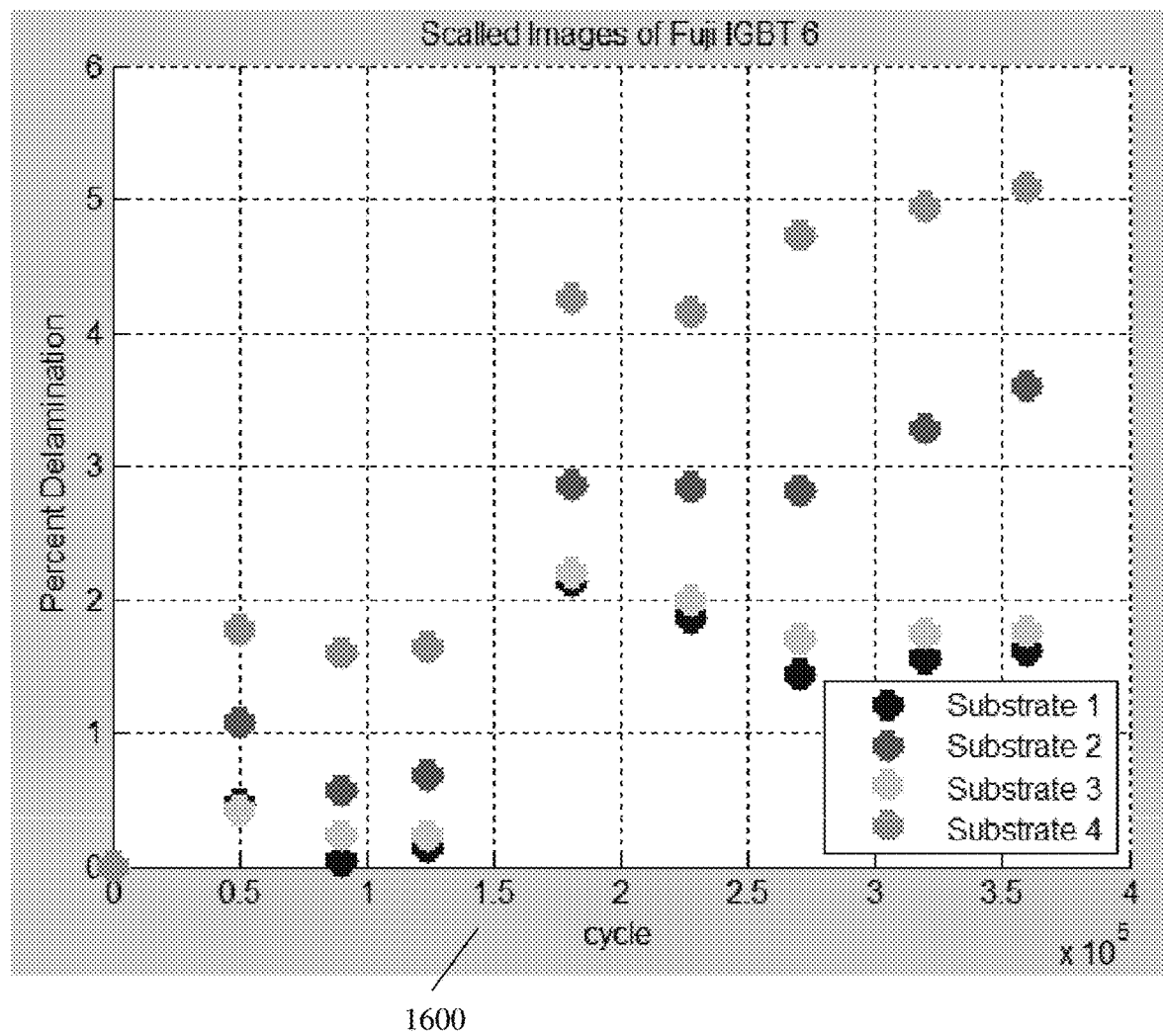
FIG. 16 is a plot of the percentage of delamination vs. number of cycles for a Fuji IGBT in accordance with some aspects of the present disclosure.

At 426, the delamination percentage for the IGBT, may be presented to the user, e.g., via display 118. For example, in some aspects, the delamination percentage may be presented as a numerical value or other indication of a percentage of delamination. In some aspects, the delamination percentage for the IGBT over time, number of cycles, or other similar measures may be plotted, e.g., as shown in plots 1100 and 1600 of FIGS. 11 and 16, respectively.

The data shown in the plots 1100 and 1600 was generated by cycling both PowerEx and Fuji IGBTs many thousands of times with CSAM images taken periodically over the course of the test. The plots provide visibility into how quickly the delamination happens over a known duty cycle. This method may also be used to examine parts in the field that have been in use for a number of years to show what a particular OEM or drive cycle will have on the devices life.

For example, as seen in plot 1100, the calculated percentage of delamination in the Powerex IGBT increased as the number of cycles increased, especially for the first substrate. For example, after approximately 180,000 cycles, the delamination for substrate 1 was 6%, after approximately 225,000 cycles the delamination jumped to approximately 9%, etc. Similar results can be seen in plot 1600 where some substrates exhibited greater delamination than others in the Fuji IGBT.

At 428, if any additional IGBT images are remaining, the method returns to step 402 and loads the next grey scale image into memory. If there are no remaining IGBT images, the method ends and presents the results to a user of computing device 110, e.g., via display 118. For example, the overlay composite image generated at 422 and delamination percentage determined at 424 may be presented to the user on display 118 as illustrated, for example, in the image overlay FIGS. 10 and 15.

In some aspects, the changes to the percentage delamination of the IGBT may be used to monitor or predict the remaining life of the IGBT or other IGBTs being used in a similar manner. For example, an IGBT installed on a vehicle or other device may be monitored over its life cycle, e.g., by taking CSAM images of the IGBT during routine maintenance or at other opportunities. The changes to the percentage of delamination for each successive CSAM image may be assessed to determine the life cycle of the IGBT for this active vehicle or device and predict when this IGBT may fail. For example, if successive CSAM images show that the rate of delamination is increasing or the percentage of delamination for the IGBT is trending toward a pre-determined threshold at which the IGBT is determined to have failed, a predicted end of life for the IGBT may be determined, e.g., based on the trend of the percentage delamination data. In some aspects, for example, the IGBT may be scheduled to be removed from service at or prior to the predicted end of life, e.g., at or prior to the point when the percentage delamination reaches the pre-determined threshold. For example, the service schedule for a particular vehicle or device may be updated such that a regularly scheduled service appointment for the vehicle or device that is prior to predicted failure of the IGBT may be modified to include replacement of the IGBT. In some aspects, the last regularly scheduled service appointment for the vehicle or device prior to predicted failure of the IGBT may be modified to include replacement of the IGBT. In some aspects, a new service appointment may be generated for the vehicle or device prior to the predicted failure of the IGBT to replace the IGBT.

In some aspects, the percentage delamination data for the IGBT may be leveraged to reliably assess the life cycle of similar IGBTs installed on other vehicles or devices, e.g., other vehicles or devices performing a similar function or located in a similar region. For example, successive CSAM images of the IGBT of the other vehicle or device may also be analyzed to determine a percentage of delamination which may be compared to the IGBT delamination data of the original.

In some aspects, percentage delamination for each successive CSAM image of an IGBT installed in a vehicle or device may be examined and correlated to a generic vehicle power management system (VPMS) duty cycle analysis. This may allow the remaining life of the IGBT to be predicted.

In some aspects, the percentage delamination data for the IGBT may be used to refine the generic VPMS duty cycle for usage across all original equipment manufacturers (OEMs). This information may be used to analyze new OEMs and their IGBT duty cycles to predict a life expectancy for the new IGBTs.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed:

1. A method of determining delamination in a transistor, the method implemented by at least one processor comprising hardware, the method comprising:
    loading a grey scale image of a transistor into memory;
    generating a black and white image based on the loaded grey scale image;
    identifying boundaries within the generated black and white image that have a size equal to or greater than a pre-determined size;
    cropping the black and white image based on the identified boundaries to generate a cropped black and white image;
    identifying at least one feature in the cropped black and white image based on the identified boundaries;
    normalizing the cropped black and white image based on an attribute of the identified at least one feature;
    cropping the grey scale image based on the normalized black and white image;
    comparing the cropped grey scale image to a baseline grey scale image of the transistor; and
    determining a change in a percentage of delamination of the transistor between the baseline grey scale image and the cropped grey scale image based on the comparison.

2. The method of claim 1, further comprising generating a plot of the change in percentage of delamination; and presenting the plot to a user via a display.

3. The method of claim 1,
wherein generating the black and white image based on the loaded grey scale image comprises generating a first black and white image by applying a first grey level threshold to the grey scale image, and
wherein identifying boundaries within the generated black and white image comprises identifying boundaries within the generated first black and white image,
the method further comprising:
   determining that the number of identified boundaries for the first black and white image is greater than a pre-determined threshold number of boundaries;
   generating a second black and white image based on the loaded grey scale image by applying a second grey level threshold to the grey scale image; and
   identifying boundaries within the generated second black and white image that have at least the pre-determined size.

4. The method of claim 3, wherein the second grey level threshold is determined based on the Otsu Grey-Level Threshold technique.

5. The method of claim 3, wherein cropping the black and white image based on the identified boundaries comprises cropping the generated second black and white image based on the identified boundaries within the generated second black and white image.

6. The method of claim 3, further comprising:
determining that the number of identified boundaries for the second black and white image is greater than the pre-determined threshold number of boundaries;
generating a third black and white image based on the loaded grey scale image by applying a third grey level threshold to the grey scale image; and
identifying boundaries within the generated third black and white image that have at least the pre-determined size.

7. The method of claim 6, wherein cropping the black and white image based on the identified boundaries comprises cropping the generated third black and white image based on the identified boundaries within the generated third black and white image.

8. The method of claim 1, further comprising updating a service schedule for an apparatus including the transistor based on the determined change in the percentage of delamination of the transistor between the baseline grey scale image and the cropped grey scale image.

9. The method of claim 1, wherein normalizing the cropped black and white image based on an attribute of the identified at least one feature comprises calculating an area of the identified at least one feature and normalizing the cropped black and white image based on the calculated area.

10. The method of claim 1, wherein determining the change in the percentage of delamination of the transistor between the baseline grey scale image and the cropped grey scale image based on the comparison comprises:
   calculating a first area of a substrate in the cropped grey scale image, the substrate corresponding to one of the identified boundaries;
   calculating a second area of a corresponding substrate in the baseline grey scale image; and
   determining based on the calculated first and second areas a percentage of delamination of the substrate in the cropped grey scale image relative to the corresponding substrate in the baseline grey scale image.

11. A non-transitory computer readable medium comprising instructions for determining delamination in a transistor that, when executed by at least one processor comprising hardware, configure the at least one processor to:
   load a grey scale image of a transistor into memory;
   generate a black and white image based on the loaded grey scale image;
   identify boundaries within the generated black and white image that have a size equal to or greater than a pre-determined size;
   crop the black and white image based on the identified boundaries to generate a cropped black and white image;
   identify at least one feature in the cropped black and white image based on the identified boundaries;
   normalize the cropped black and white image based on an attribute of the identified at least one feature;
   crop the grey scale image based on the normalized black and white image;
   compare the cropped grey scale image to a baseline grey scale image of the transistor; and
   determine a change in a percentage of delamination of the transistor between the baseline grey scale image and the cropped grey scale image based on the comparison.

12. The non-transitory computer readable medium of claim 11, wherein the instructions further configure the at least one processor to:
   generate a plot of the change in percentage of delamination; and
   present the plot to a user via a display.

13. The non-transitory computer readable medium of claim 11,
wherein generating the black and white image based on the loaded grey scale image comprises generating a first black and white image by applying a first grey level threshold to the grey scale image,
wherein identifying boundaries within the generated black and white image comprises identifying boundaries within the generated first black and white image, and
wherein the instructions further configure the at least one processor to:
   determine that the number of identified boundaries for the first black and white image is greater than a pre-determined threshold number of boundaries;
   generate a second black and white image based on the loaded grey scale image by applying a second grey level threshold to the grey scale image; and
   identify boundaries within the generated second black and white image that have at least the pre-determined size.

14. The non-transitory computer readable medium of claim 13, wherein the second grey level threshold is determined based on the Otsu Grey-Level Threshold technique.

15. The non-transitory computer readable medium of claim 13, wherein cropping the black and white image based on the identified boundaries comprises cropping the generated second black and white image based on the identified boundaries within the generated second black and white image.

16. The non-transitory computer readable medium of claim 13, the instructions further configuring the at least one processor to:
   determine that the number of identified boundaries for the second black and white image is greater than the pre-determined threshold number of boundaries;
   generate a third black and white image based on the loaded grey scale image by applying a third grey level threshold to the grey scale image; and identify boundaries within the generated third black and white image that have at least the pre-determined size, wherein cropping the black and white image based on the identified boundaries comprises cropping the generated third black and white image based on the identified boundaries within the generated third black and white image.

17. The non-transitory computer readable medium of claim 11, the instructions further configuring the at least one processor to update a service schedule for an apparatus including the transistor based on the determined change in the percentage of delamination of the transistor between the baseline grey scale image and the cropped grey scale image.

18. The non-transitory computer readable medium of claim 11, wherein normalizing the cropped black and white image based on an attribute of the identified at least one feature comprises calculating an area of the identified at least one feature and normalizing the cropped black and white image based on the calculated area.

19. The non-transitory computer readable medium of claim 11, wherein determining the change in the percentage of delamination of the transistor between the baseline grey scale image and the cropped grey scale image based on the comparison comprises:

calculating a first area of a substrate in the cropped grey scale image, the substrate corresponding to one of the identified boundaries;

calculating a second area of a corresponding substrate in the baseline grey scale image; and determining based on the calculated first and second areas a percentage of delamination of the substrate in the cropped grey scale image relative to the corresponding substrate in the baseline grey scale image.

20. A system comprising:

at least one processor comprising hardware; and memory storing instructions for determining delamination in a transistor that, when executed by the at least one processor, configure the at least one processor to:

load a grey scale image of a transistor into memory;

generate a black and white image based on the loaded grey scale image;

identify boundaries within the generated black and white image that have a size equal to or greater than a pre-determined size;

crop the black and white image based on the identified boundaries to generate a cropped black and white image;

identify at least one feature in the cropped black and white image based on the identified boundaries;

normalize the cropped black and white image based on an attribute of the identified at least one feature;

crop the grey scale image based on the normalized black and white image;

compare the cropped grey scale image to a baseline grey scale image of the transistor; and determine a change in a percentage of delamination of the transistor between the baseline grey scale image and the cropped grey scale image based on the comparison.

* * * * *